United States Patent [19]

Panoz et al.

[11] Patent Number: 4,721,619

[45] Date of Patent: Jan. 26, 1988

[54] CONTROLLED ABSORPTION DILTIAZEN PHARMACEUTICAL FORMULATION

[75] Inventors: Donald E. Panoz, Whale Bay, Bermuda; Edward J. Geoghegan, Athlone, Ireland

[73] Assignee: Elan Corporation p.l.c., Ireland

[21] Appl. No.: 684,661

[22] Filed: Dec. 20, 1984

[30] Foreign Application Priority Data

Dec. 22, 1983 [IE] Ireland .................................. 3057/83

[51] Int. Cl.$^4$ .......................... A61K 9/50; A61K 9/58
[52] U.S. Cl. ..................................... 424/459; 424/462; 424/468; 424/473; 424/490; 424/497; 514/965
[58] Field of Search .................... 424/19, 20, 22, 468, 424/473, 459, 462, 490, 497; 514/965

[56] References Cited

U.S. PATENT DOCUMENTS

| | | | |
|---|---|---|---|
| 3,965,255 | 6/1976 | Bloch et al. | 424/472 |
| 4,230,687 | 10/1980 | Sair et al. | 514/965 |
| 4,263,273 | 4/1981 | Appelgren et al. | 424/19 |
| 4,361,546 | 11/1982 | Stricker et al. | 424/462 |
| 4,499,066 | 2/1985 | Moro et al. | 424/22 |
| 4,555,399 | 11/1985 | Hsiao | 424/80 |
| 4,592,753 | 6/1986 | Panoz | 604/897 |
| 4,600,645 | 7/1986 | Ghebre-Sellassie et al. | 424/19 |
| 4,609,542 | 9/1986 | Panoz et al. | 424/19 |
| 4,610,870 | 9/1986 | Jain et al. | 424/19 |

FOREIGN PATENT DOCUMENTS

| | | |
|---|---|---|
| 0013262 | 7/1980 | European Pat. Off. |
| 0077956 | 5/1983 | European Pat. Off. |
| 2313915 | 1/1977 | France |
| 59-10512A | 1/1984 | Japan |
| 2039737 | 8/1980 | United Kingdom .................. 424/19 |

OTHER PUBLICATIONS

Chemical Abstracts, vol. 100, No. 18, Apr. 30, 1984, p. 367.

*Primary Examiner*—Ronald W. Griffin
*Attorney, Agent, or Firm*—Hubbard, Thurman, Turner & Tucker

[57] ABSTRACT

A controlled absorption diltiazem formulation for oral administration comprises a pellet having a core of diltiazem or a pharmaceutically acceptable salt thereof in association with an organic acid and a lubricant, and an outer membrane which permits release of diltiazem in an aqueous medium at a controlled rate which is substantially pH independent. The pellet has a dissolution rate in vitro, which when measured according to the Paddle Method of U.S. Pharmacopoeia XX, is not more than 10% of the total diltiazem after 2 hours of measurement in a buffered medium. Not more than 30% of the total diltiazem is released after a total of 4 hours measurement and not more than 40% of the total diltiazem is released after a total of 6 hours. 100% release is achieved after 12 hours, with a maximum of 80% of the total diltiazem being released after 8 hours.

10 Claims, 2 Drawing Figures

CONTROLLED ABSORPTION DILTIAZEN PHARMACEUTICAL FORMULATION

BACKGROUND OF THE INVENTION

1. Field of the Invention

This invention relates to a controlled absorption pharmaceutical formulation and, in particular, to a controlled absorption form of diltiazem for oral administration.

2. Description of the Prior Art

Diltiazem-cis-(+)-3-(acetyloxy)-5-[2-(dimethylamino)ethyl]-2,3-dihydro-2-(4-methoxyphenyl)-1,5-benzothiazepin-4(5H)-one, is a benzothiazine derivative possessing calcium antagonist activity. Diltiazem has been shown to be useful in alleviating symptoms of chronic heart disease, particularly angina pectoris and myocardial ischemia while displaying a low incidence of side effects. Diltiazem is conventionally administered in normal capsule form as diltiazem hydrochloride sold under the Trade Mark Cardiazem (Marion Laboratories Inc.).

Conventional diltiazem therapy starts with 30 mg administered 4 times daily. The dosage is gradually increased to 240 mg, given in divided doses three or four times daily, at one- to two-day intervals until an optimum response is obtained. Diltiazem is extensively metabolized by the liver and excreted by the kidneys and in bile. According to professional use information issued by Marion Laboratories Inc., diltiazem is absorbed from the known tablet formulation (Cardiazem) to about 80% and is subject to an extensive first-pass effect, giving an absolute bioavailability, compared to intravenous administration, of about 40%. Single oral doses of 30 to 120 mg of diltiazem result in peak plasma levels 2–3 hours after administration. Detectable plasma levels occur within 30–60 minutes after administration indicating that diltiazem is readily absorbed.

The plasma elimination half-life following single or multiple administration is approximately 3–5 hours. Therapeutic blood levels of diltiazem are thought to be in the range of 50–200 ng/ml.

An article by McAuley, Bruce. J. and Schroeder, John S. in Pharmacotherapy 2: 121, 1982, states that peak plasma levels of diltiazem occur within 1 hour with normal capsules and within 3 to 4 hours with sustained release tablets.

It is an object of the present invention to provide a controlled absorption diltiazem formulation suitable for twice daily administration and which has improved bioavailability relative to known diltiazem oral formulations.

SUMMARY OF THE INVENTION

Accordingly, the invention provides a controlled absorption diltiazem formulation for oral administration, comprising a pellet having a core of diltiazem or a pharmaceutically acceptable salt thereof in association with organic acid and a lubricant, and an multi-layer membrane surrounding said core and containing a major proportion of a pharmaceutically acceptable film forming, water insoluble polymer and a minor proportion of a pharmaceutically acceptable film forming, water soluble polymer, the number of layers in said membrane and the ratio of said water soluble polymer to water insoluble polymer being effective to permit release of said diltiazem from said pellet at a rate allowing controlled absorption thereof over a twelve hour period following oral administration, said rate being measured in vitro as a dissolution rate of said pellet which is substantially pH independent which when measured in a basket assembly according to U.S. Pharmacopoeia XX substantially corresponds to the following dissolution pattern:

(a) from 0 to 10% of the total diltiazem is released after 2 hours of measurement;

(b) from 10 to 30% of the total diltiazem is released after 4 hours of measurement;

(c) from 20 to 40% of the total diltiazem is released after 6 hours of measurement;

(d) from 50 to 80% of the total diltiazem is released after 8 hours of measurement; and (e) from 85 to 100% of the total diltiazem is released after 12 hours of measurement.

DESCRIPTION OF THE PREFERRED EMBODIMENTS

Preferably, the organic acid is represented by one or more of the following acids: fumaric acid, malic acid and succinic acid. The diltiazem and organic acid are preferably present in a ratio of from 19:1 to 1:1.

Preferably, the lubricant is represented by one or more of the following: sodium stearate, magnesium stearate or talc. The diltiazem and lubricant are preferably present in a ratio of from 5:1 to 100:1.

Preferably, the core comprises diltiazem or a pharmaceutically acceptable salt thereof and the associated organic acid and lubricant embedded in a pharmaceutically acceptable polymeric material in a multi-layer arrangement. The polymeric material in which the diltiazem is embedded may be rapidly soluble in water or, alternatively, be readily permeable or porous to diltiazem and water.

The polymeric material contains a major proportion of a water soluble polymer and a minor proportion of a water insoluble polymer. The ratio of water soluble to water insoluble polymer is determined by the particular combination of polymers selected. The ratio of water soluble polymer to water insoluble polymer will normally be in the range of 1.0:1 to 19:1.

The water soluble polymer is suitably polyvinyl alcohol, polyvinylpyrrolidone, hydroxypropylmethylcellulose or a polymer sold under the Trade Mark Eudragit RL or a mixture thereof.

The water insoluble polymer is suitably polyvinyl choride, shellac, polyurethane, ethylcellulose or a polymer sold under the Trade Mark Eudragit RS or a mixture thereof.

Eudragit polymers are polymeric lacquer substances based on acrylate and methacrylate. Polymers sold under the Trademark Eudragit RL and RS are resins comprising copolymers of acrylic and methacrylic acid esters with a low content of quaternary ammonium groups and are described in the "Eudragit" brochure of Rohm Pharma GmbH (1982) wherein detailed physical-chemical data of these products is given. The ammonium groups are present as salts and give rise to permeability of the lacquer films. Eudragit RL and RS are freely permeable (RL) or slightly permeable (RS), respectively independent of pH.

The term water-soluble polymer as used herein includes polymers which are freely permeable to water such as Eudragit RL. Likewise, the term water-insoluble polymer as used herein includes polymers which are slightly permeable to water such as Eudragit RS.

The core suitably has between 50 and 200 layers and is built up in a manner known per se.

Further, preferably, the multi-layer arrangement of diltiazem, organic acid, lubricant and polymeric material is built up on a central inert core suitably consisting of a non-pareil seed of starch/sugar having an average diameter in the range 0.5–0.8 mm, especially 0.6–0.71 mm, in a conventional coating pan.

The diltiazem, organic acid, lubricant and optionally other components are blended to form a homogenous powder. Alternate layers of a coating solution of the polymeric material and the powder are applied to the central inert core so as to build up the multi-layer arrangement of the active core. The concentration of the polymeric material in the coating solution is determined by the viscosity of the final solution. Preferably, between 25 and 75 parts of inert core are used relative to the homogenous powder.

The outer membrane preferably has a major proportion of a water insoluble polymer and a minor proportion of a water soluble polymer, the ratio of water insoluble to water soluble polymer being determined by the inherent solubility characteristics of the polymers selected. Preferably the ratio of water soluble polymer to water insoluble polymer is from 1:1 to 1:19.

Suitable examples of water insoluble polymers are those specified for the polymeric material referred to above or a mixture thereof. Examples of suitable water soluble polymers are also those specified for the polymeric material referred to above or a mixture thereof.

The outer membrane may also be composed of a major proportion of a non-porous polymer and a minor proportion of a porous polymer, the ratio of non-porous to porous polymer being determined by the inherent porosity of the respective polymers.

The outer membrane is built up by applying a plurality of coats of a membrane polymer solution to the active core as hereinafter described to a thickness sufficient to obtain the desired dissolution rate of the finished pellet. The membrane solution contains the polymers dissolved in a suitable solvent, optionally in the presence of other additives such as a lubricant and/or a plasticizer. Suitable lubricants are talc, magnesium stearate and sodium stearate. A suitable plasticizer is diethylphthalate.

Preferably, the number of coats of membrane solution applied is between 20 and 40. The dissolution rate achieved is proportionally slower as the number of membrane coats increases.

Further, preferably, 2–25 ml of membrane solution is applied per kilogram of active cores.

The pellets may be filled into hard gelatin capsules.

The invention will be further illustrated by the following examples.

EXAMPLE 1

Diltiazem hydrochloride (1.0 kg), fumaric acid (0.25 kg) and talc (0.100 kg) were blended and milled through a No. 100 mesh screen so as to obtain a homogenous powder.

The powder was applied to starch/sugar seeds (0.6–0.71 mm diameter) (0.5 kg) in a standard coating pan using a coating solution of:

| | |
|---|---|
| 10% Polyvinylpyrrolidone in isopropanol | 75 Parts |
| 5% Ethylcellulose in methanol/ methylene chloride 50/50 | 20 Parts |
| 5% Polyvinyl chloride in acetone. | 5 Parts |

The seeds were coated with a measured volume of coating solution followed by dusting on of a measured weight of the powder mix. The coated seeds were allowed to dry and the coating step repeated until all of the powder had been applied. The coated seeds were then dried at 45° C. overnight to remove all traces of solvent.

The coated seeds defining the active core of the pellets being prepared were then surrounded by an outer membrane by applying 35 coats of a solution consisting of:

| | |
|---|---|
| 5% Eudragit RS in acetone/ isopropanol 40/60 | 80 Parts by volume |
| 5% Eudragit RL in acetone/ isopropanol 40/60 | 15 Parts by volume |
| 5% Polyvinyl chloride in acetone | 5 Parts by volume |
| Talc | 100 Parts by weight |

Each coat of membrane solution comprised 5 ml of solution per kg of coated seeds. After each coat had been applied the pellets were air dried in the coating pan.

The finished pellets were then subjected to a dissolution test. Prior to performing the dissolution test the pellets were dried at 45° C. to evaporate all of the solvent.

The dissolution rate of the pellets was tested by the method of U.S. Pharmacopoeia XX (Paddle Method) in buffered media at pH 1.5, pH 4.0 and pH 7.0. The dissolution rate, which was found to be substantially pH independent, was as follows:

| Time (h) | % release pH 1.5 | % release pH 4.0 | % release pH 7.0 |
|---|---|---|---|
| 2 | 6.6 | 7.4 | 8.2 |
| 4 | 13.5 | 14.7 | 19.7 |
| 6 | 24.5 | 23.3 | 36.0 |
| 8 | 52.7 | 53.5 | 64.6 |
| 12 | 97.4 | 93.6 | 95.0 |

EXAMPLE 2

Example 1 was repeated except that the coating solution used was:

| | |
|---|---|
| 7.5% Polyvinylpyrrolidone in isopropanol | 80 Parts |
| 17.5% Shellac in ethanol | 20 Parts |

The membrane solution used was:

| | |
|---|---|
| 7.5% Polyvinylpyrrolidone in isopropanol | 10 Parts by volume |
| 17.5% Shellac in ethanol | 90 Parts by volume |
| Isopropanol | 100 Parts by volume |
| Talc | 100 Parts by weight. |

The dissolution rate of the pellets, which was measured according to the procedure followed in Example 1, was found to be:

| Time (h) | % release pH 1.5 | % release pH 4.0 | % release pH 7.0 |
| --- | --- | --- | --- |
| 2 | 6.4 | 8.3 | 9.7 |
| 4 | 12.9 | 15.7 | 21.4 |
| 6 | 27.2 | 25.8 | 37.7 |
| 8 | 58.5 | 51.2 | 67.7 |
| 12 | 94.6 | 90.9 | 97.6 |

EXAMPLE 3

Pellets according to Example 1 were filled directly into hard gelatin capsules without the addition of any extra ingredients so as to obtain capsules containing 60 mg of of diltiazem hydrochloride.

EXAMPLE 4

Pellets according to Example 2 were filled directly into hard gelatin capsules without the addition of any extra ingredients so as to obtain capsules containing 120 mg diltiazem hydrochloride.

BIOAVAILABILITY DATA diltiazem in capsule form according to Example 3 (+) compared with a single dose (60 mg) of diltiazem in a loose filled capsule (*). The graphs of FIG. 1 were drawn from the mean values obtained for six subjects according to the data listed in Table 1 on day 5 of administration.

FIG. 2 is a graph of plasma levels (ng/ml) versus time after administration (hours) for a single dose (120 mg) of diltiazem in capsule form according to Example 4 (+) compared with a single dose (60 mg) of diltiazem in a loose filled capsule (*). The graphs of FIG. 2 were drawn from the mean values obtained for eight subjects according to the data listed in Table 2.

Both the single dose (FIG. 2; Table 2) and steady state (FIG. 1; Table 1) bioavailability data illustrate the suitability of the diltiazem formulation according to the invention as a twice per day form of diltiazem. As will be observed from Table 3 below, the products of Examples 3 and 4 are bioequivalent to the reference loose-filled capsule (i.e. there is no loss in AUC). The diltiazem formulation according to the invention, as exemplified by the products of Examples 3 and 4, shows a prolonged plasma profile with a delayed peaking time, lower peak plasma levels and a lower peak-to-trough plasma fluctuation both on single dose and steady state.

TABLE 1

Steady State Study
Plasma Levels ng/ml

| | HOURS AFTER ADMINISTRATION | | | | | | | | | | | | | |
| --- | --- | --- | --- | --- | --- | --- | --- | --- | --- | --- | --- | --- | --- | --- |
| SUBJ | 0.00 | 0.00 | 1.00 | 2.00 | 3.00 | 4.00 | 5.00 | 6.00 | 7.00 | 8.00 | 9.00 | 10.00 | 11.00 | 12.00 | AVG |
| DILTIAZEM - 60 mg loose-filled capsules | | | | | | | | | | | | | | |
| 1 | 0.00 | 33.40 | 171.00 | 141.60 | 133.50 | 85.30 | 62.70 | 59.00 | 51.60 | 48.00 | 41.70 | 34.10 | 29.50 | 38.70 | 874.05 |
| 2 | 0.00 | 21.80 | 54.50 | 88.30 | 88.60 | 83.70 | 68.50 | 55.70 | 42.60 | 32.60 | 20.50 | 18.30 | 20.40 | 12.90 | 591.05 |
| 3 | 0.00 | 22.30 | 120.50 | 94.90 | 75.00 | 52.60 | 44.40 | 37.70 | 31.60 | 28.30 | 24.40 | 16.40 | 15.40 | 14.20 | 559.45 |
| 4 | 0.00 | 16.40 | 117.70 | 108.00 | 73.30 | 53.50 | 39.50 | 36.10 | 31.10 | 24.30 | 22.60 | 18.80 | 15.10 | 14.20 | 543.45 |
| 5 | 0.00 | 37.30 | 34.80 | 78.50 | 78.10 | 71.90 | 49.00 | 49.20 | 37.70 | 34.40 | 33.70 | 25.80 | 21.80 | 19.80 | 1070.60 |
| 6 | 0.00 | 57.70 | 48.00 | 45.90 | 92.50 | 147.40 | 177.60 | 135.00 | 103.10 | 89.50 | 71.70 | 56.50 | 53.50 | 42.10 | |
| MEAN | 0.00 | 31.48 | 91.08 | 92.87 | 86.83 | 82.40 | 73.62 | 62.12 | 49.62 | 42.85 | 35.77 | 28.32 | 25.95 | 23.65 | 698.98 |
| ST DEV | 0.00 | 15.04 | 53.52 | 31.75 | 15.14 | 34.84 | 52.12 | 36.89 | 27.29 | 24.23 | 19.32 | 15.28 | 14.48 | 13.24 | 221.23 |
| CV (%) | 0.00 | 47.76 | 58.76 | 34.19 | 17.43 | 42.28 | 70.80 | 59.38 | 55.00 | 56.54 | 54.02 | 53.95 | 55.81 | 55.96 | 31.65 |
| DILTIAZEM - as per Example 3 | | | | | | | | | | | | | | |
| 1 | 0.00 | 59.10 | 53.20 | 46.10 | 51.60 | 66.50 | 73.30 | 84.90 | 74.10 | 101.00 | 97.70 | 83.30 | 70.80 | 52.30 | 858.20 |
| 2 | 0.00 | 33.90 | 30.60 | 30.60 | 36.70 | 39.70 | 38.10 | 41.80 | 59.30 | 56.00 | 39.00 | 33.70 | 29.50 | 23.80 | 469.90 |
| 3 | 0.00 | 23.40 | 20.60 | 21.10 | 19.70 | 21.10 | 22.50 | 26.20 | 47.90 | 59.50 | 54.20 | 38.80 | 33.90 | 23.80 | 389.10 |
| 4 | 0.00 | 26.90 | 32.00 | 18.10 | 20.90 | 24.70 | 26.90 | 26.90 | 30.40 | 33.30 | 36.20 | 47.90 | 32.90 | 30.70 | 359.00 |
| 5 | 0.00 | 22.40 | 18.50 | 17.30 | 23.10 | 26.80 | 30.80 | 34.70 | 45.80 | 56.90 | 61.70 | 49.40 | 38.80 | 43.10 | 436.55 |
| 6 | 0.00 | 148.50 | 150.70 | 119.20 | 101.50 | 86.60 | 97.70 | 106.70 | 116.70 | 136.30 | 171.90 | 156.90 | 161.00 | 123.20 | 1540.35 |
| MEAN | 0.00 | 52.37 | 50.93 | 42.07 | 42.25 | 43.07 | 48.48 | 51.85 | 59.45 | 74.38 | 79.57 | 69.22 | 61.85 | 50.43 | 675.52 |
| ST DEV | 0.00 | 49.02 | 50.40 | 39.31 | 31.50 | 26.97 | 30.23 | 34.10 | 31.52 | 37.38 | 49.39 | 45.98 | 50.70 | 37.12 | 461.07 |
| CV (%) | 0.00 | 93.60 | 98.96 | 93.44 | 74.55 | 62.62 | 62.35 | 64.53 | 53.02 | 50.25 | 62.08 | 66.43 | 81.98 | 73.60 | 68.25 |

*Area under the curve
**Coefficient of variation

Description of the Drawings

FIG. 1 is a graph of plasma levels (ng/ml) versus time after administration (hours) for a single dose (60 mg) of

TABLE 2

Plasma Levels (ng/ml)

Figure 1:
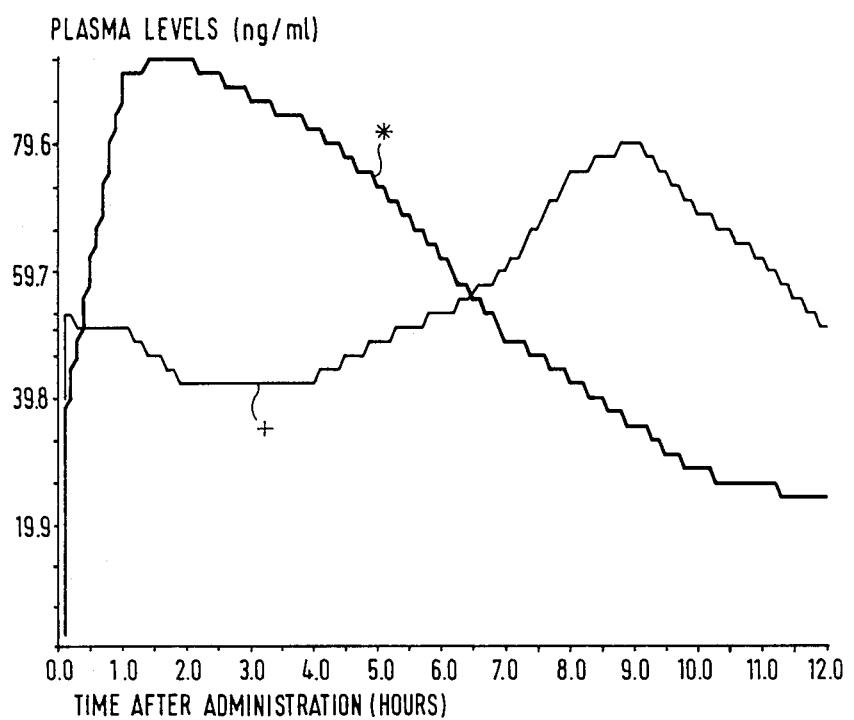
Figure 2:
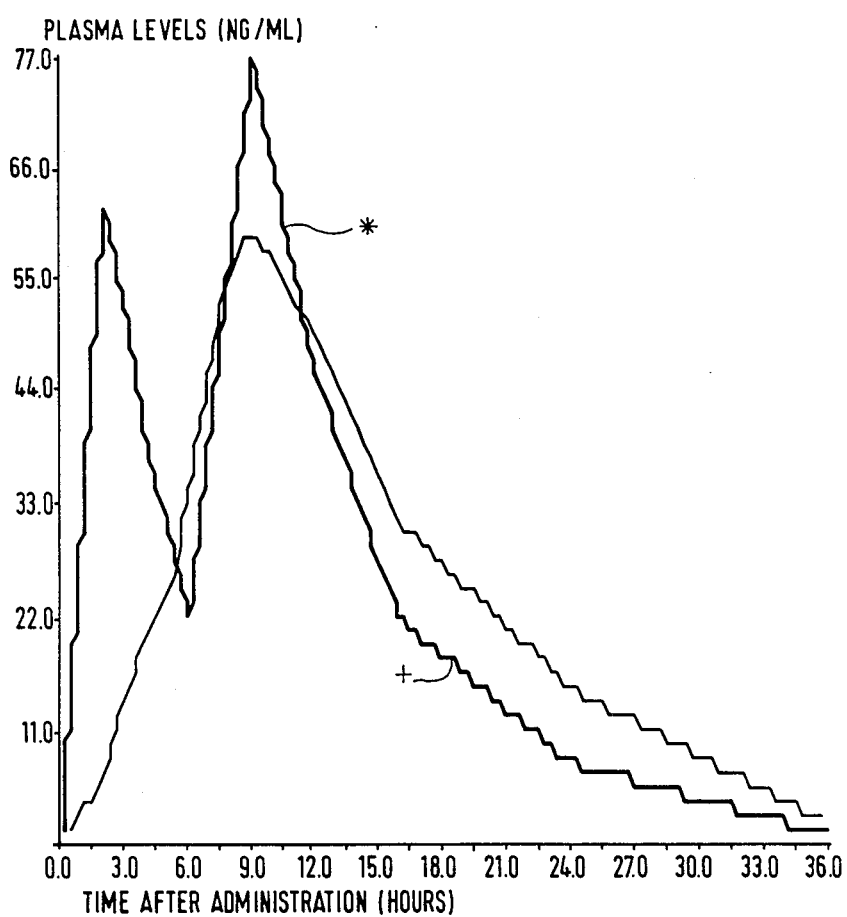

| | HOURS AFTER ADMINISTRATION | | | | | | | | | | | | | |
| --- | --- | --- | --- | --- | --- | --- | --- | --- | --- | --- | --- | --- | --- | --- |
| SUBJ | 0.00 | 2.00 | 3.00 | 4.00 | 5.00 | 6.00 | 8.00 | 9.00 | 10.00 | 11.00 | 12.00 | 16.00 | 24.00 | 36.00 | AUC* |
| DILTIAZEM - loose-filled capsule 60 mg at 0 and 6 hours | | | | | | | | | | | | | | |
| 1 | 0.00 | 20.00 | 39.00 | 30.00 | 24.00 | 17.00 | 36.00 | 62.00 | 52.00 | 41.00 | 33.00 | 18.00 | 10.00 | 0.00 | 648.00 |
| 2 | 0.00 | 51.00 | 30.00 | 20.00 | 22.00 | 14.00 | 68.00 | 54.00 | 41.00 | 30.00 | 23.00 | 10.00 | 0.00 | 0.00 | 514.00 |
| 3 | 0.00 | 60.00 | 42.00 | 33.00 | 26.00 | 19.00 | 58.00 | 54.00 | 51.00 | 45.00 | 38.00 | 20.00 | 7.00 | 0.00 | 741.50 |
| 4 | 0.00 | 149.00 | 118.00 | 80.00 | 60.00 | 44.00 | 102.00 | 154.00 | 138.00 | 124.00 | 105.00 | 53.00 | 23.00 | 8.00 | 1975.00 |
| 5 | 0.00 | 40.00 | 50.00 | 44.00 | 36.00 | 29.00 | 28.00 | 65.00 | 58.00 | 49.00 | 37.00 | 15.00 | 0.00 | 0.00 | 630.00 |
| 6 | 0.00 | 76.00 | 60.00 | 49.00 | 38.80 | 25.00 | 78.00 | 97.00 | 79.00 | 65.00 | 56.00 | 26.00 | 8.00 | 0.00 | 1032.50 |

TABLE 2-continued

| | Plasma Levels (ng/ml) HOURS AFTER ADMINISTRATION | | | | | | | | | | | | | | |
|---|---|---|---|---|---|---|---|---|---|---|---|---|---|---|---|
| SUBJ | 0.00 | 2.00 | 3.00 | 4.00 | 5.00 | 6.00 | 8.00 | 9.00 | 10.00 | 11.00 | 12.00 | 16.00 | 24.00 | 36.00 | AUC* |
| 7 | 0.00 | 58.00 | 37.00 | 26.00 | 21.00 | 17.00 | 26.00 | 49.00 | 61.00 | 50.00 | 42.00 | 18.00 | 7.00 | 0.00 | 678.50 |
| 8 | 0.00 | 53.00 | 42.00 | 28.00 | 21.00 | 16.00 | 78.00 | 81.00 | 52.00 | 39.00 | 30.00 | 14.00 | 7.00 | 0.00 | 712.00 |
| MEAN | 0.00 | 63.38 | 52.25 | 38.75 | 31.00 | 22.63 | 59.25 | 77.00 | 66.50 | 55.38 | 45.50 | 21.75 | 7.75 | 1.00 | 866.50 |
| ST DEV | 0.00 | 38.21 | 28.03 | 19.17 | 13.47 | 9.98 | 27.34 | 34.96 | 30.90 | 29.51 | 25.90 | 13.47 | 7.17 | 2.83 | 471.92 |
| CV (%) | 0.00 | 60.29 | 53.65 | 49.48 | 43.45 | 44.13 | 46.14 | 45.40 | 46.46 | 53.30 | 56.91 | 61.92 | 92.47 | 282.84 | 54.46 |
| | DILTIAZEM - as per Example 4 120 mg at 0 hours | | | | | | | | | | | | | | |
| 1 | 0.00 | 0.00 | 6.00 | 11.00 | 13.00 | 20.00 | 42.00 | 46.00 | 42.00 | 36.00 | 35.00 | 23.00 | 9.00 | 0.00 | 562.50 |
| 2 | 0.00 | 7.00 | 10.00 | 11.00 | 13.00 | 17.00 | 24.00 | 24.00 | 33.00 | 29.00 | 28.00 | 19.00 | 13.00 | 6.00 | 542.00 |
| 3 | 0.00 | 0.00 | 10.00 | 15.00 | 26.00 | 44.00 | 60.00 | 52.00 | 44.00 | 39.00 | 35.00 | 23.00 | 11.00 | 0.00 | 677.50 |
| 4 | 0.00 | 20.00 | 29.00 | 35.00 | 38.00 | 58.00 | 133.00 | 157.00 | 163.00 | 156.00 | 140.00 | 86.00 | 40.00 | 10.00 | 2220.50 |
| 5 | 0.00 | 0.00 | 14.00 | 22.00 | 31.00 | 42.00 | 53.00 | 49.00 | 46.00 | 47.00 | 39.00 | 26.00 | 10.00 | 0.00 | 705.00 |
| 6 | 0.00 | 0.00 | 7.00 | 10.00 | 14.00 | 27.00 | 43.00 | 43.00 | 41.00 | 39.00 | 40.00 | 30.00 | 15.00 | 0.00 | 689.00 |
| 7 | 0.00 | 15.00 | 25.00 | 34.00 | 38.00 | 43.00 | 47.00 | 41.00 | 35.00 | 33.00 | 31.00 | 20.00 | 12.00 | 0.00 | 681.00 |
| 8 | 0.00 | 7.00 | 12.00 | 16.00 | 16.00 | 25.00 | 59.00 | 62.00 | 55.00 | 47.00 | 44.00 | 23.00 | 10.00 | 0.00 | 692.50 |
| MEAN | 0.00 | 6.13 | 14.13 | 19.25 | 23.63 | 34.50 | 57.63 | 59.25 | 57.38 | 53.25 | 49.00 | 31.25 | 15.00 | 2.00 | 846.25 |
| ST DEV | 0.00 | 7.77 | 8.41 | 10.17 | 11.02 | 14.31 | 32.54 | 40.95 | 43.21 | 41.98 | 37.12 | 22.38 | 10.28 | 3.85 | 558.25 |
| CV (%) | 0.00 | 126.90 | 59.53 | 52.81 | 46.64 | 41.49 | 56.47 | 69.11 | 75.31 | 78.84 | 75.75 | 71.63 | 68.54 | 192.72 | 66.03 |

*Area under the curve
**Coefficient of variation

TABLE 3

| | Single Dose | | Steady State (Day 5) | |
|---|---|---|---|---|
| | Loose-filled reference capsule | Product of Example 4 | Loose-filled reference capsule | Product of Example 3 |
| AUC* (ng h/ml) | 957 | 925 | 699 | 676 |
| Tmax (h)** | 2.8 | 8.7 | 2.2 | 8.7 |
| Cmax (ng/ml)*** | 86.5 | 71.2 | 125.7 | 83.5 |
| Cmax/C trough**** | 3.9 | 1.6 | 9.3 | 4.3 |

*Area under curve.
**Time to maximum blood concentration.
***Maximum blood concentration.
****Ratio of Cmax to concentration at dosing time.

The bioavailability studies indicate that the diltiazem formulation according to the invention is an effective twice daily form of diltiazem.

What we claim is:

1. A controlled absorption diltiazem formulation for oral administration, comprising a pellet having a core of diltiazem or a pharmaceutically acceptable salt thereof in association with an organic acid and a lubricant, and a multi-layer membrane surrounding said core and containing a major proportion of a pharmaceutically acceptable film forming, water insoluble polymer and a minor proportion of a pharmaceutically acceptable film forming, water soluble polymer, the number of layers in said membrane and the ratio of said water soluble polymer to water insoluble polymer being effective to permit release of said diltiazem from said pellet at a rate allowing controlled absorption thereof over a twelve hour period following oral administration, said rate being measured in vitro as a dissolution rate of said pellet which is substantially pH independent, which when measured in a basket assembly according to U.S. Pharmacopoeia XX substantially corresponds to the following dissolution pattern:
   (a) from 0 to 10% of the total diltiazem is released after 2 hours of measurement;
   (b) from 10 to 30% of the total diltiazem is released after 4 hours of measurement;
   (c) from 20 to 40% of the total diltiazem is released after 6 hours of measurement;
   (d) from 50 to 80% of the total diltiazem is released after 8 hours of measurement; and
   (e) from 85 to 100% of the total diltiazem is released after 12 hours of measurement.

2. A formulation according to claim 1, wherein the organic acid is selected from the group consisting of one or more of the following acids: fumaric acid, malic acid and succinic acid, the diltiazem and organic acid being present in a ratio of from 19:1 to 1:1.

3. A formulation according to claim 2, wherein the lubricant is selected from the group consisting of one or more of sodium stearate, magnesium stearate and talc and the diltiazem and the lubricant are present in a ratio of from 5:1 to 100:1.

4. A formulation according to claim 3, wherein the core comprises:
   (a) a powder mixture comprising diltiazem or a pharmaceutically acceptable salt thereof, an organic acid selected from the group consisting of fumaric acid, malic acid and succinic acid, and said lubricant, and
   (b) a polymeric material comprising a major proportion of a pharmaceutically acceptable water soluble polymer and a minor proportion of a pharmaceutically acceptable water insoluble polymer, said core comprising layers of said powder mixture and said polymeric material superimposed one upon the other wherein said polymeric material is present in an amount sufficient to ensure that all of said powder mixture is coated into said core.

5. A formulation according to claim 4, wherein the pharmaceutically acceptable water soluble polymer is selected from the group consisting of polyvinyl alcohol, polyvinylpyrrolidone and hydroxypropylmethylcellulose.

6. A formulation according to claim 4, wherein the pharmaceutically acceptable water insoluble polymer is selected from the group consisting of polyvinylchloride, shellac, polyurethane and ethylcellulose.

7. A formulation according to claim 1, wherein the water insoluble polymer of the membrane is selected from the group consisting of polyvinylchloride, shellac, polyurethane and ethylcellulose and the water soluble polymer is selected from the group consisting of polyvinyl alcohol, polyvinylpyrrolidone and hydroxypropylmethylcellulose.

8. A formulation according to claim 4, wherein the polymeric material of the core comprises a major proportion of a copolymer of acrylic and methacrylic acid esters which is freely permeable to water and a minor proportion of a copolymer of acrylic and methacrylic acid esters which is slightly permeable to water.

9. A formulation according to claim 1 wherein the multi-layer membrane consists of a major proportion of a copolymer of acrylic and methacrylic acid esters which is slightly permeable to water and a minor proportion of a copolymer of acrylic and methacrylic acid esters which is freely permeable to water.

10. A capsule comprising pellets according to claim 1.

* * * * *